United States Patent [19]
Saito et al.

[11] Patent Number: 5,736,614
[45] Date of Patent: Apr. 7, 1998

[54] PERFLUORO UNSATURATED NITRILE COMPOUND AND PROCESS FOR PRODUCING THE SAME

[75] Inventors: Satoru Saito; Riichi Iwa; Haruyoshi Tatsu, all of Ibaraki, Japan; Rondarev Dmitrii Stefanovich; Sokolov Sergey Vasilyevich, both of Saint Petersburg, Russian Federation; Berenblit Vsevolod Vulfovich, Leningradskaya oblast, Russian Federation

[73] Assignees: Nippon Mektron Limited, Tokyo, Japan; The Central Synthetic Rubbers Research Institute, Saint Petersburg, Russian Federation

[21] Appl. No.: 732,132

[22] Filed: Oct. 18, 1996

Related U.S. Application Data

[62] Division of Ser. No. 544,198, Oct. 17, 1995, abandoned.

[30] Foreign Application Priority Data

Nov. 4, 1994 [JP] Japan .................................. 6-295548

[51] Int. Cl.$^6$ .................. C08F 120/42; C08F 214/20; C07C 255/10; C07C 255/11
[52] U.S. Cl. ................... 525/326.4; 525/331.2; 526/245; 526/247; 558/380; 558/382
[58] Field of Search ................... 558/380, 382; 525/326.4, 331.2; 526/245, 247

[56] References Cited

U.S. PATENT DOCUMENTS

| | | | |
|---|---|---|---|
| 3,933,767 | 1/1976 | Nottke | 526/245 |
| 4,138,426 | 2/1979 | England | 260/465.6 |
| 4,281,092 | 7/1981 | Breazeale | 526/245 |

FOREIGN PATENT DOCUMENTS

| | | |
|---|---|---|
| 0 174 614 | 3/1986 | European Pat. Off. |
| 0 708 139 A1 | 4/1996 | European Pat. Off. |
| 1145445 | 3/1969 | United Kingdom |

OTHER PUBLICATIONS

*Chemical Abstracts* vol. 113, No. 9, 1990; A.A. Machuls et al., Rodiochemical Alkylation of Adamantanes by Perfluorovinyl Ethers, p. 725.

*Angew. Chem. Int. Ed. Engl.* vol. 24 (1985) Hans Milauer et al, Hexafluoropropene Oxide–A Key Compound in Organofluorine Chemistry, pp. 161–179.

*Primary Examiner*—Johann Richter
*Assistant Examiner*—Jane C. Oswecki
*Attorney, Agent, or Firm*—Barnes & Thornburg

[57] ABSTRACT

A perfluoro unsaturated nitrile compound represented by the following general formula:

$$CF_2=CFO(CF_2)_nOCF(CF_3)CN$$

is produced by reaction of chlorine or bromine to a perfluoro unsaturated carboxylic acid ester represented by the following general formula:

$$CF_2=CFO(CF_2)_nOCF(CF_3)COOR$$

followed by reaction with ammonia, thereby converting the ester group to an acid amide group, and then conducting a dehydration reaction and a dehalogenation reaction of the resulting perfluoro unsaturated carboxylic acid amide represented by the following general formula:

$$CF_2=CFO(CF_2)_nOCF(CF_3)CONH_2$$

in any desired sequence, and is effectively applied as a cross-linking site monomer for fluorine-containing elastomers.

8 Claims, 7 Drawing Sheets

PERFLUORO UNSATURATED NITRILE COMPOUND AND PROCESS FOR PRODUCING THE SAME

This is a continuation of application Ser. No. 08/544,198, filed Oct. 17, 1995, abandoned.

BACKGROUND OF THE INVENTION

1. Field of the Invention

The present invention relates to a perfluoro unsaturated nitrile compound and a process for producing the same, and more particularly to a novel perfluoro unsaturated nitrile compound effectively applicable as a cross-linking site monomer for fluorine-containing elastomers or the like and a process for producing the same.

2. Related Art

U.S. Pat. No. 3,933,767 discloses a perfluoro unsaturated nitrile compound represented by the following general formula:

$$CF_2=CFOCF_2[CF(CF_3)OCF_2]_nCF(CF_3)CN$$

where n is 0~4, and U.S. Pat. No. 4,281,092 discloses a perfluoro unsaturated nitrile compound represented by the following general formula:

$$CF_2=CF[OCF_2CF(CF_3)]_nO(CF_2)_mCN$$

where n is 1~2 and m is 1~4.

These perfluoro unsaturated nitrile compounds(nitrile group-containing perfluorovinylethers) have been used as crosslinking site monomers for fluorine-containing elastomer copolymers by copolymerizing the perfluoro unsaturated nitrile compounds into the fluorine-containing elastomers.

SUMMARY OF THE INVENTION

An object of the present invention is to provide a perfluoro unsaturated nitrile compound having a different structure from those of the so far known perfluoro unsaturated nitrile compounds(nitrile group-containing perfluorovinylethers), which can be effectively applied likewise as a cross-linking site monomer for the fluorine-containing elastomers.

According to the present invention, there is provided a novel perfluoro unsaturated nitrile compound represented by the following general formula:

$$CF_2=CFO(CF_2)_nOCF(CF_3)CN$$

where n is 2, 3, 4 or 5.

DETAILED DESCRIPTION OF THE INVENTION

The present novel perfluoro unsaturated nitrile compound can be synthesized through any one of the following three synthesis routes (A),(B) and(C).

Synthesis route (A)

Perfluoro unsaturated carboxylic acid ester represented by the following general formula:

$$CF_2=CFO(CF_2)_nOCF(CF_3)COOR$$

where R is an alkyl group having 1 to 10 carbon atoms and n is an integer of 2 to 5, is subjected to addition reaction of chlorine or bromine onto the vinyl group of the ester to obtain a halogenated perfluoro saturated carboxylic acid ester represented by the following general formula:

$$CF_2XCFXO(CF_2)_nOCF(CF_3)COOR$$

where R and n have the same meanings as defined above and X is a chlorine atom or a bromine atom. Then, the thus obtained halogenated perfluoro saturated carboxylic acid ester is reacted with ammonia to convert the ester group to an acid amide group to obtain an acid amide represented by the following general formula:

$$CF_2XCFXO(CF_2)_nOCF(CF_3)CONH_2$$

where X and n have the same meanings as defined above. Then, the acid amide is dehalogenated to form a vinyl group again and a unsaturated acid amide represented by the following general formula is obtained:

$$CF_2=CFO(CF_2)_nOCF(CF_3)CONH_2$$

where n has the same meaning as defined above. Then, the resulting unsaturated acid amide is dehydrated to obtain a desired product.

The starting material for the synthesis route (A), i.e. perfluoro unsaturated carboxylic acid ester can be obtained by reacting a dicarboxylic acid fluoride represented by the following general formula:

$$FOC(CF_2)_{n-2}COF$$

where n is an integer of 2, 3, 4 or 5, with hexafluoropropene oxide to obtain a dicarboxylic acid difluoride represented by the following general formula [Angew. Chem. Int. Ed. 24, 161~179(1985)]:

$$FOCCF(CF_3)O(CF_2)_nOCF(CF_3)COF$$

where n has the same meaning as defined above, and then by reacting only one acid fluoride group of the resulting dicarboxylic acid difluoride with alcohol to monoesterify the dicarboxylic acid difluoride to obtain a compound represented by the following general formula:

$$FOCCF(CF_3)O(CF_2)_nOCF(CF_3)COOR$$

where n has the same meaning as defined above and R is an alkyl group having 1 to 10 carbon atoms, and then by subjecting the other remaining carboxylic acid fluoride group to a FCOF-releasing reaction.

In the addition reaction of halogen to the thus obtained perfluoro unsaturated carboxylic acid ester, chlorine or bromine is used as a halogen, where bromine is preferable from the viewpoint of easy handling and easy reaction controllability. The addition reaction of halogen can be carried out even in the absence of a solvent, but preferably in the presence of a solvent. Any solvent can be used, so long as it can solve the raw materials and is inert to halogen. Preferably, a fluorine-containing solvent such as 1,1,2-trichloro-1,2,2-trifluoroethane (F-113), perfluoro(2-butyltetrahydrofuran), perfluorohexane, etc. can be used. To activate the addition reaction, the reaction can be also carried out under irradiation of light such as sun beams, ultraviolet lamp light, etc. in the presence of a fluorine-containing solvent.

Reaction of halogenated perfluoro saturated carboxylic acid ester with ammonia can be carried out even in the absence of a solvent, but preferably in the presence of such a solvent as used in the addition reaction of halogen. The reaction can be carried out under the atmospheric pressure or under pressure.

Formation of vinyl group by dehalogenation reaction of the halogenated perfluoro saturated carboxylic acid amide is carried out in a protic polar solvent such as methanol, ethanol, etc. or an aprotic polar solvent such as dioxane, tetrahydrofuran, etc. in the presence of a dehalogenating agent such as Zn, Zn/ZnCl$_2$, Zn/ZnBr$_2$, Zn/Cu, Mg, etc. Zn can be used after activation of the surface with dilute hydrochloric acid, etc.

Conversion of the carboxylic acid amide group to the nitrile group can be carried out with a dehydrating agent such as phosphorus pentoxide in the presence or absence of an inert solvent at a reaction temperature of about 100° to 300° C. The conversion can be also carried out with trifluoroacetic acid anhydride and pyridine in an aprotic solvent such as dioxane, diglyme, tetrahydrofuran, etc. at not more than room temperature.

Synthesis route (B)

The starting material, perfluoro unsaturated carboxylic acid ester, is directly reacted with ammonia and the resulting perfluoro unsaturated carboxylic acid amide is subjected to a dehydration reaction to obtain a desired product.

The reaction of perfluoro unsaturated carboxylic acid ester with ammonia can be carried out in the same manner as in the reaction with ammonia in the above-mentioned Synthesis route (A). Since the perfluorovinyl group ($CF_2$=CF—) is not protected in that case, there is a possibility of side reaction to form an NC—CHF— group. Thus it is necessary to control reaction conditions, particularly to keep the amount of ammonia equimolar to the raw material ester.

Dehydration reaction of the resulting perfluoro unsaturated carboxylic acid is carried out in the same manner as in the above-mentioned Synthesis route (A).

Synthesis route (C)

Addition reaction of halogen to the starting material, perfluoro unsaturated carboxylic acid ester, and successive reaction with ammonia are carried out in the same manner as in the above-mentioned Synthesis route (A), and then the thus obtained halogenated perfluoro saturated carboxylic acid amide is subjected to a dehydration reaction to obtain a nitrile compound represented by the following general formula:

$$CF_2XCFXO(CF_2)nOCF(CF_3)CN$$

where X is a chlorine atom or a bromine atom and n is an integer of 2, 3, 4 or 5, and the resulting nitrile compound is subjected to a dehalogenation reaction to obtain a desired product.

The dehydration reaction and dehalogenation reaction are carried out in the same manner as in the above-mentioned Synthesis route (A).

According to the present invention, a novel perfluoro unsaturated nitrile compound(nitrile group-containing perfluorovinylether) can be provided and can be effectively applied as a cross-linking site monomer for fluorine-containing elastomers.

PREFERRED EMBODIMENTS OF THE INVENTION

The present invention will be explained in detail below, referring to Examples.

EXAMPLE 1

[Synthesis route (C)]

(1) 422 g of methyl perfluoro(2-methyl-3,7-dioxa-8nonanoate) having the following chemical formula:

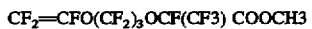

and 300 g of F-113 were charged into a three-necked glass flask having a net capacity of 1 liter, provided with a stirrer, a dropping funnel and a cooling pipe, and 160 g of bromine was dropwise added thereto from the dropping funnel over one hour, while keeping the flask inside at 40° C. After the dropwise addition, the resulting reaction mixture was washed successively with an aqueous 5% sodium hydrogen sulfite solution and water. The organic layer was dried over magnesium sulfated, filtered and distilled, whereby 582 g of methyl perfluoro (2-methyl-3,7-dioxa-8,9-dibromo-8-nonanoate) was obtained(yield: 100% ).

Boiling point: 87°~88° C. (5 Torr), $d_4^{20}$:1.8801, $n_D^{20}$:1.3510

Figure 1:
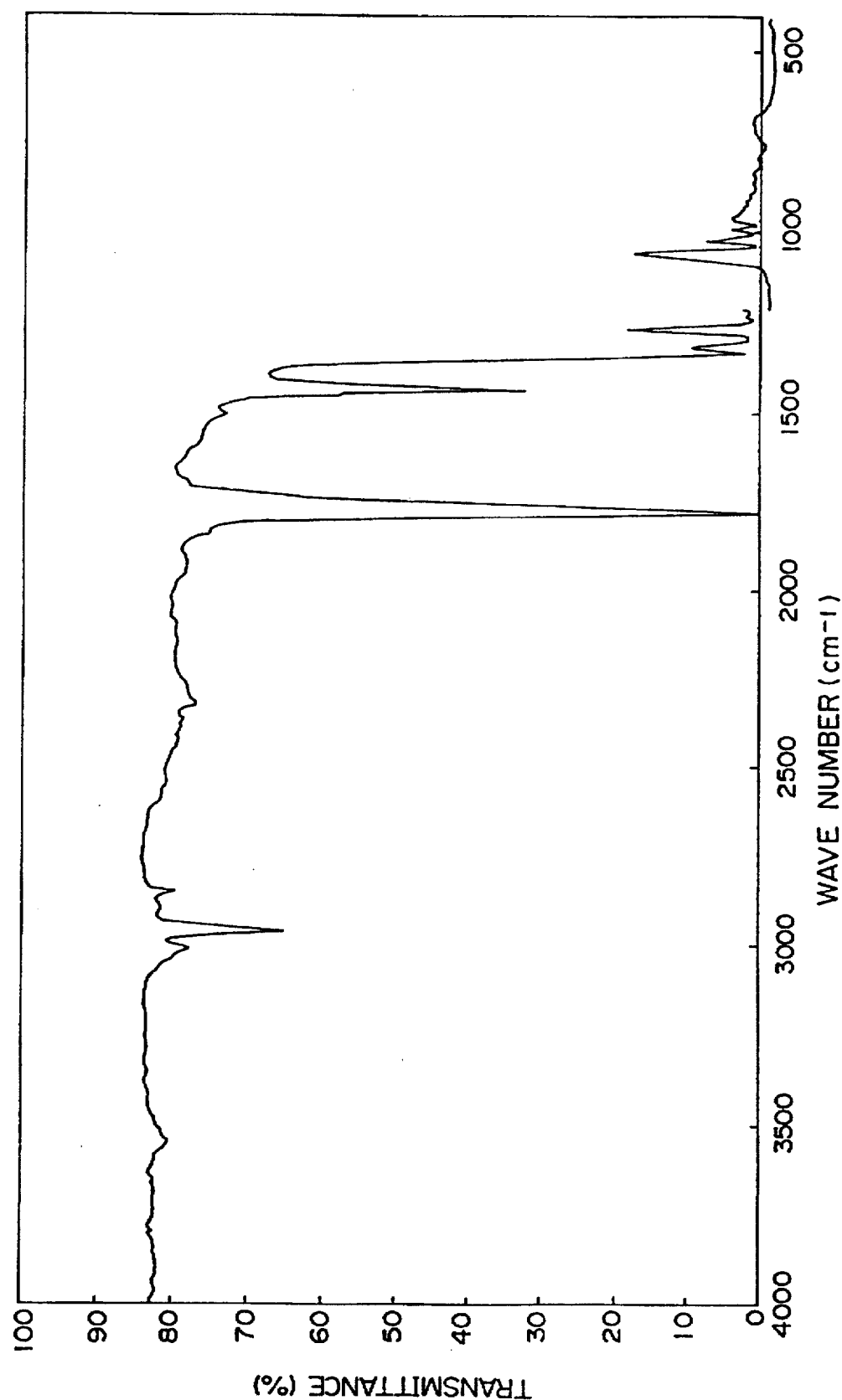
FIG. 1 is a diagram showing infrared absorption spectra of methyl perfluoro(2-methyl-3,7-dioxa-8,9-dibromo-8-nonanoate).

Infrared absorption spectra: see FIG. 1 $^{19}$F-NMR(internal standard: CFCl$_3$):

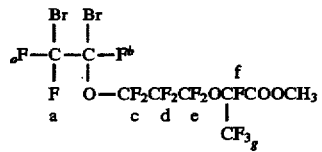

a = −60.7 ppm
b = −68.5
c = −83.5
d = −126.7
e = −76.1, −79.8
f = −128.9
g = −80.1

(2) 582 g of the thus obtained methyl-perfluoro (2-methyl-3, 7-dioxa-8,9-dibromo-8-nonanoate) and 400 g of F-113 were charged into a three-necked glass flask having a net capacity of 1 liter, provided with a stirrer, a gas feed tube and a dry ice cooling pipe, and 20 g of ammonia gas was slowly introduced into the flask with stirring, while keeping the flask inside at a lower temperature than 30° C. After heat release was finished in the flask, stirring was further continued for 8 hours. Then, the solvent, ammonia and formed methanol were removed from the flask by distillation in reduced pressure, and then the residues were further distilled in reduced pressure, whereby 540 g of perfluoro (2-methyl-3,7-dioxa-8,9-dibromo-8-nonanamide) having a melting point of 70°~75° C. was obtained as white crystals (yield: 95%).

(3) 540 g of the thus obtained perfluoro (2-methyl-3,7-dioxa-8,9-dibromo-8-nonanamide) and 250 g of phosphorus pentoxide were mixed together, pulverized and charged into a glass flask having a net capacity of 2 liters. After heating at 160°~170° C. for 10 hours, the reaction mixture was distilled in reduced pressure, and the resulting crude product was further distilled under reduced pressure while keeping a small amount of phosphorus pentoxide therein, whereby 459 g of perfluoro (2-methyl-3,7-dioxa-8,9-dibromo-8-nonanitrile) was obtained (yield: 87%).

Boiling point: 72° C. (25 Torr), $d_4^{20}$:1.9281, $n_D^{20}$:1.3382

Figure 2:
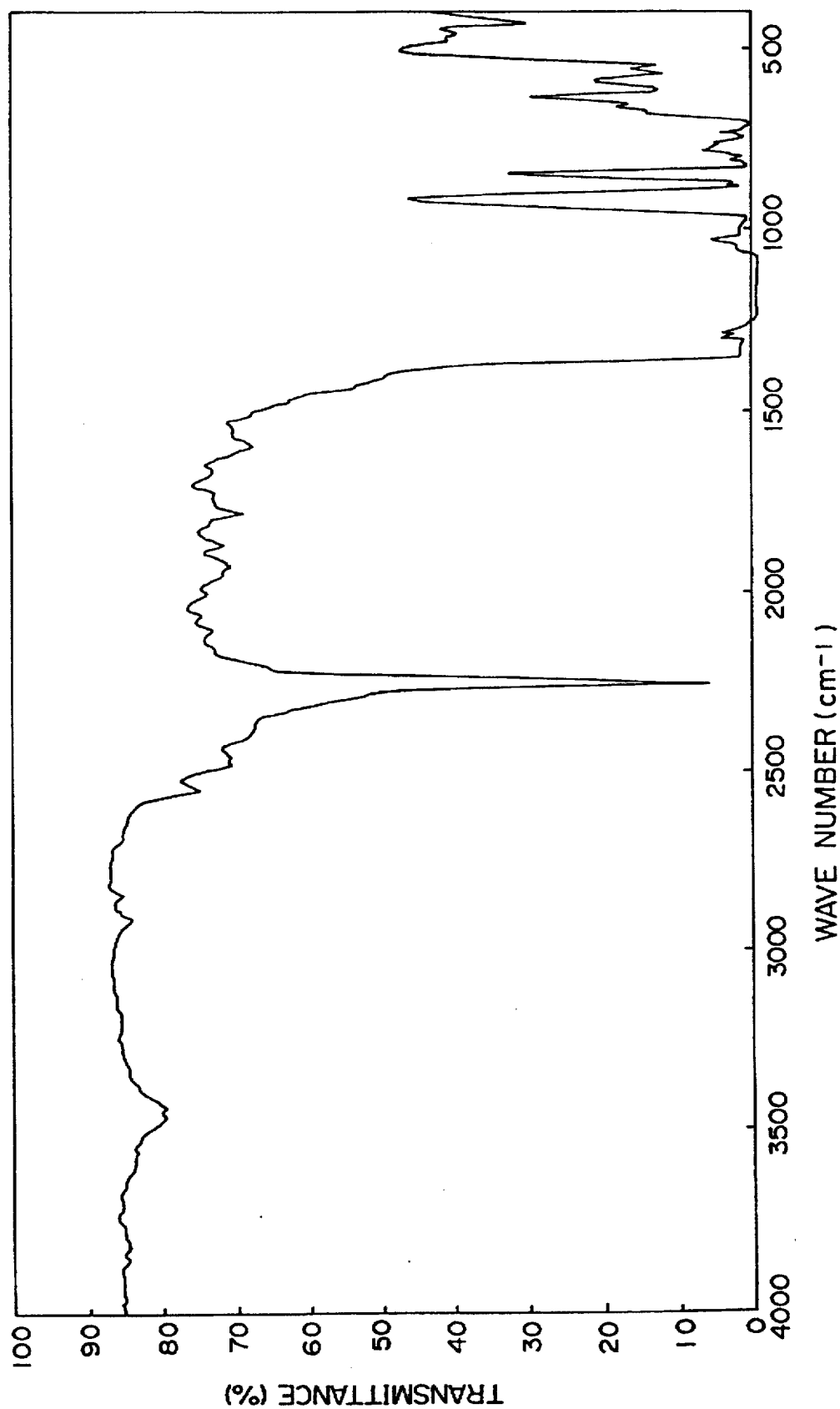
FIG. 2 is a diagram showing infrared absorption spectra of perfluoro(2-methyl-3,7-dioxa-8,9-dibromo-8-nonanitrile).

Infrared absorption spectra: see FIG. 2 $^{19}$F-NMR (internal standard: CFCl$_3$):

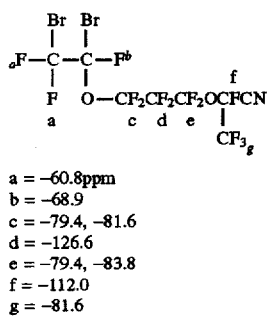

a = –60.8ppm
b = –68.9
c = –79.4, –81.6
d = –126.6
e = –79.4, –83.8
f = –112.0
g = –81.6

(4) 65 g of zinc powder, 1 g of zinc bromide and 1 liter of dioxane were charged into a four-necked glass flask having a net capacity of 2 liters, provided with a stirrer, a thermometer, a dropping funnel and a cooling pipe, and heated to the reflux temperature with vigorous stirring, and then 459 g of the thus obtained perfluoro (2-methyl-3,7-dioxa-8,9-dibromo-8-nonanitrile) was dropwise added thereto over 2 hours. After the dropwise addition, the solvent and the product mixture were removed from the flask by distillation, and the thus obtained product mixture was washed with water 4 times, and the organic layer was dried over magnesium sulfate and filtered. The thus obtained filtrate was distilled, whereby 280 g of perfluoro (2-methyl-3,7-dioxa-8-nonenonitrile) was obtained (yield: 89%).

Boiling point: 103°~104° C., $d_4^{20}$:1.5951, $n_D^{20}$:1.2870

Figure 3:
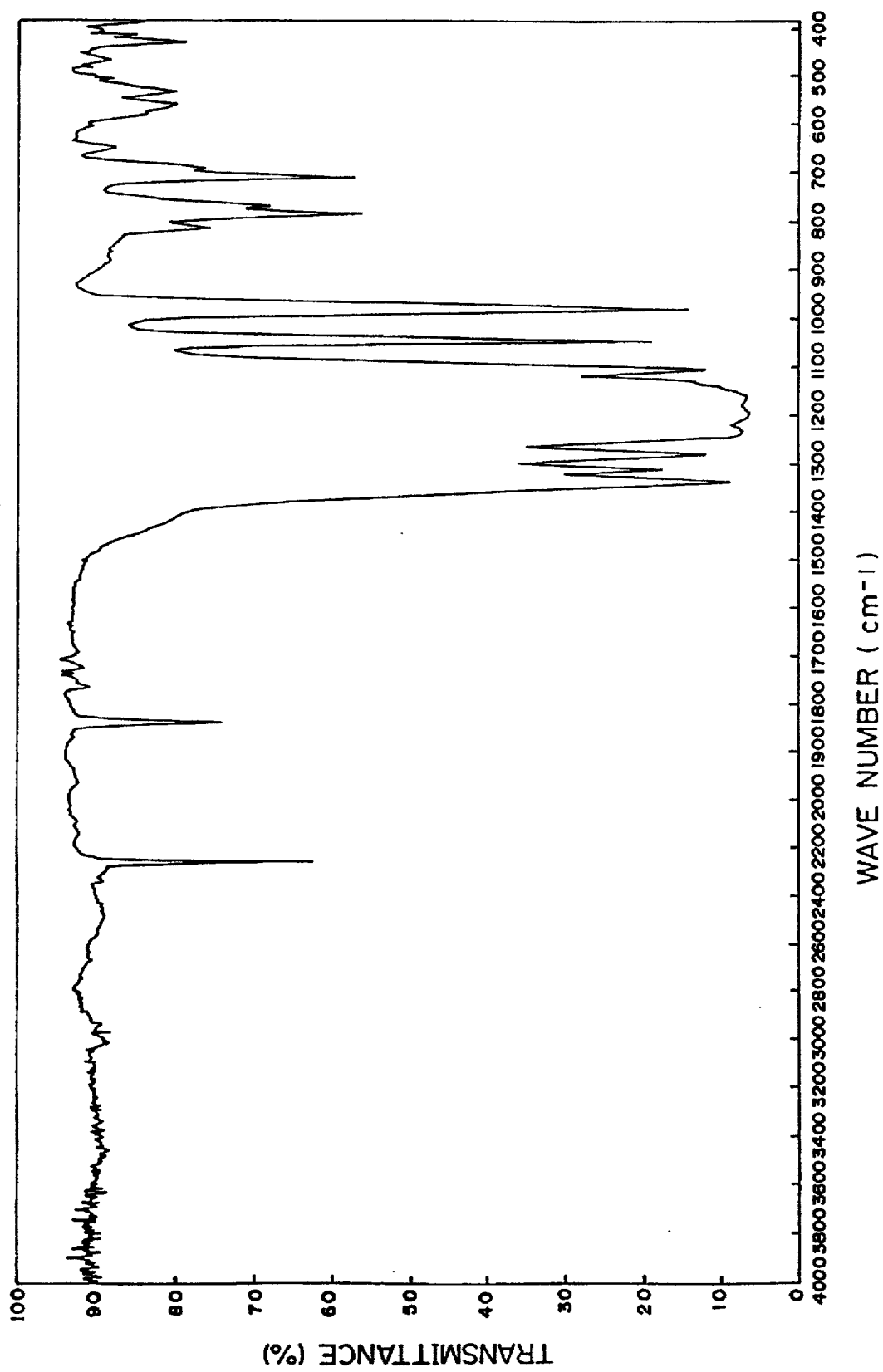
FIG. 3 is a diagram showing infrared absorption spectra of perfluoro(2-methyl-3,7-dioxa-8-nonenonitrile).

Infrared absorption spectra: see FIG. 3 $^{19}$F-NMR (internal standard: CFCl$_3$)

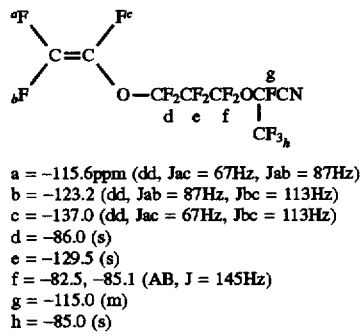

a = –115.6ppm (dd, Jac = 67Hz, Jab = 87Hz)
b = –123.2 (dd, Jab = 87Hz, Jbc = 113Hz)
c = –137.0 (dd, Jac = 67Hz, Jbc = 113Hz)
d = –86.0 (s)
e = –129.5 (s)
f = –82.5, –85.1 (AB, J = 145Hz)
g = –115.0 (m)
h = –85.0 (s)

EXAMPLE 2

[Synthesis route (B)]

(1) 118 g of methyl perfluoro (2-methyl-3,8-dioxa-9decenate) having the following chemical formula:

$$CF_2=CFO(CF_2)_4OCF(CF_3)COOCH_3$$

and 200 g of perfluoro (2-butyltetrahydrofuran) were charged into a three-necked glass flask having a net capacity of 500 ml, provided with a stirrer, a gas feed tube and a dry ice cooling pipe, and 5 g of ammonia gas was slowly introduced into the flask with stirring, while keeping the flask inside at a lower temperature than 0° C. After the ammonia addition, stirring was further continued for 3 hours, and the solvent, ammonia and formed methanol were removed therefrom by distillation under reduced pressure, whereby 80 g of crude perfluoro (2-methyl-3,8-dioxa-9-decenamide) was obtained as white crystals. It was found from infrared absorption spectra (KBr) that the white crystals were a desired product by the presence of 1711 cm$^{-1}$ (—CONH$_2$), 1841 cm$^{-1}$(C=C).

(2) 80 g of the thus prepared crude perfluoro (2-methyl-3,8-dioxa-9-decenamide) and 30 g of phosphorus pentoxide were mixed together and pulverized, and charged into a glass flask having a net capacity of 300 ml. Then, the flask was heated to 200° C. Low boiling components formed in the course of the reaction were removed from the flask by distillation through a cooling pipe. Crude residues were distilled in the presence of a small amount of phosphorus pentoxide, whereby 60 g of perfluoro (2-methyl-3,8-dioxa-9-decenonitrile) was obtained (total yield: 55%).

Boiling point: 126° C., $d_4^{20}$:1.2890, $n_D^{20}$:1.6924

EXAMPLE 3

[Synthesis route (A)]

(1) 33 g of zinc powder and 200 ml of dioxane were charged into a four-necked glass flask having a net capacity of 500 ml, provided with a stirrer, a dropping funnel and a cooling pipe, and heated to the reflux temperature with vigorous stirring. Then, 141 g of perfluoro (2-methyl-3,7-dioxa-8,9-dibromo-8-nonanamide) obtained in Example 1 (2) was dropwise added thereto. After the dropwise addition, dioxane was removed therefrom by distillation, and 200 ml of toluene was added to the residues, and the resulting mixture was heated to the reflux temperature and filtered while hot. Toluene was removed from the filtrate by distillation, whereby 61 g of crude perfluoro (2-methyl-3,7-dioxa-8-nonenamide) was obtained.

(2) 61 g of the thus obtained crude perfluoro (2-methyl-3,7-dioxa-8-nonenamide) and 21 g of phosphorus pentoxide were subjected to reaction under the same conditions as in Example 2 (2), whereby 50 g of perfluoro (2-methyl-3,7-dioxa-6nonenonitrile) was obtained (total yield: 52%).

EXAMPLE 4

[Synthesis route (C)]

(1) 150 g of methyl perfluoro (2-methyl-3,8-dioxa-9decenoate) having the following chemical formula:

$$CF_2=CFO(CF_2)_4OCF(CF_3)COOCH_3$$

was charged into a three-necked glass flask having a net capacity of 300 ml, provided with a stirrer, a dropping funnel and a cooling pipe, and 67 g of bromine was dropwise added thereto from the dropping funnel over one hour, while keeping the flask inside at 5° to 10°C. After the dropwise addition, stirring was further continued at room temperature over a night, and then the reaction mixture was washed with an aqueous 5% sodium hydrogen sulfite solution and then with water. The organic layer was dried over magnesium sulfate, filtered and distilled, whereby 171 g of methyl perfluoro (2-methyl-3,8-dioxa-9,10-dibromo-9-decanoate) was obtained (yield: 85%).

Figure 4:
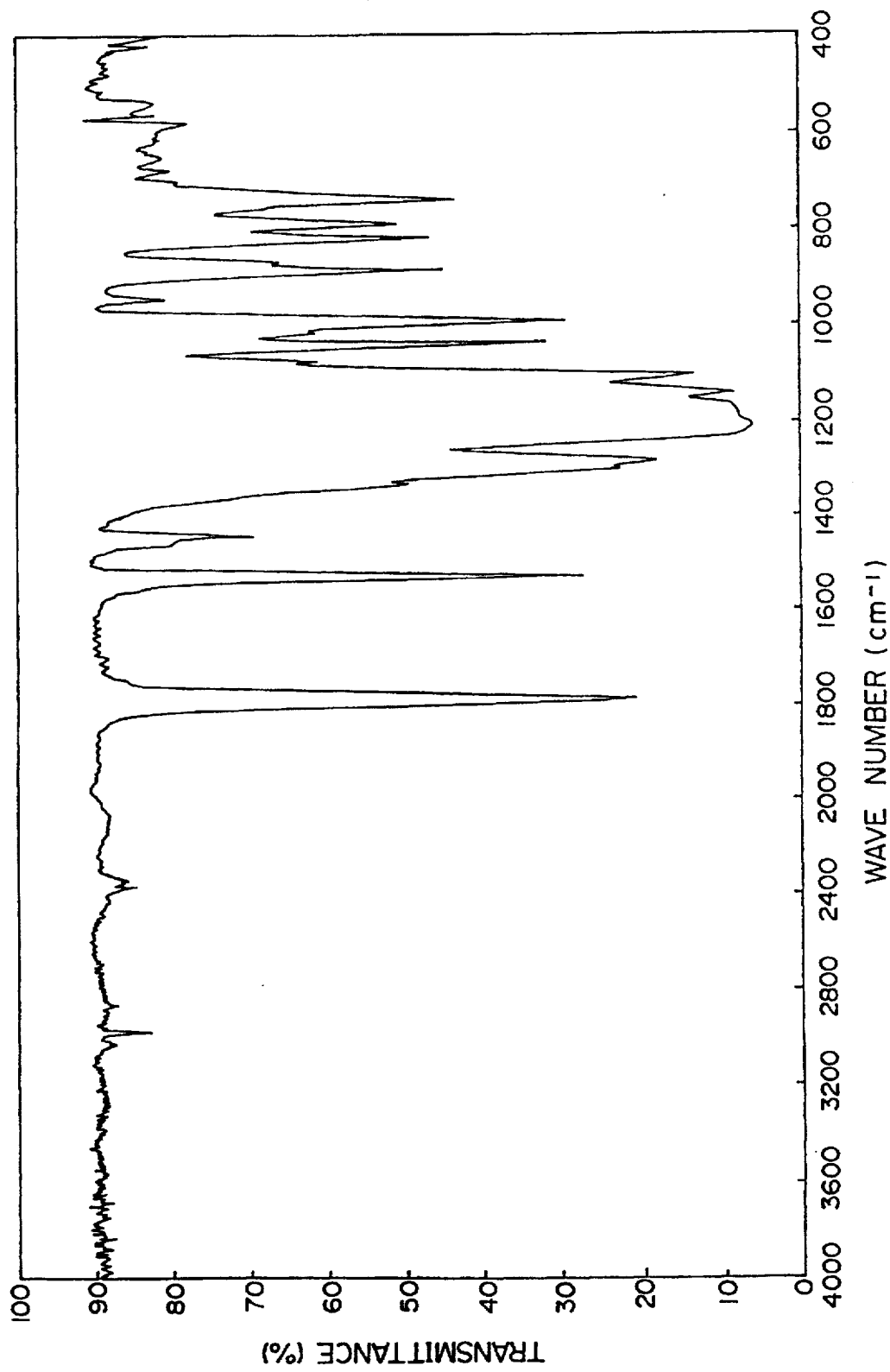
FIG. 4 is a diagram showing infrared absorption spectra of methyl perfluoro(2-methyl-3,8-dioxa-9,10-dibromo-9-decanoate).

Boiling point: 55°–57°C. (0.3 Torr)
Infrared absorption spectra: see FIG. 4
$^{19}$F-NMR (internal standard: CFCl$_3$):

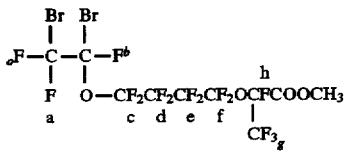

a = –62.5ppm
b = –70.2
c, f= –77.3, –79.1, –84.2, –85.9
d, e= –124.7
g = –82.0
h = –130.6

(2) 23 g of the thus obtained methyl perfluoro (2-methyl-3,8-dioxa-9,10-dibromo-8-nonanoate) and 200 ml of perfluorohexane (PF-5060, trademark of a product made by Sumitomo 3M Co., Japan) were charged into a glass flask having a net capacity of 300 ml, provided with a stirrer and a gas feed tube, and an ammonia gas was bubbled into the solution at a feed rate of 100 ml/min. for one hour with stirring, while keeping the flask inside at 5° to 10° C. Then, the solvent, ammonia and formed methanol were removed therefrom by distillation under reduced pressure, and then the residues were distilled under reduced pressure, whereby 108 g of perfluoro (2-methyl-3,8-dioxa-9,10-dibromo-9-decanamide) was obtained (yield: 90%).

Figure 5:
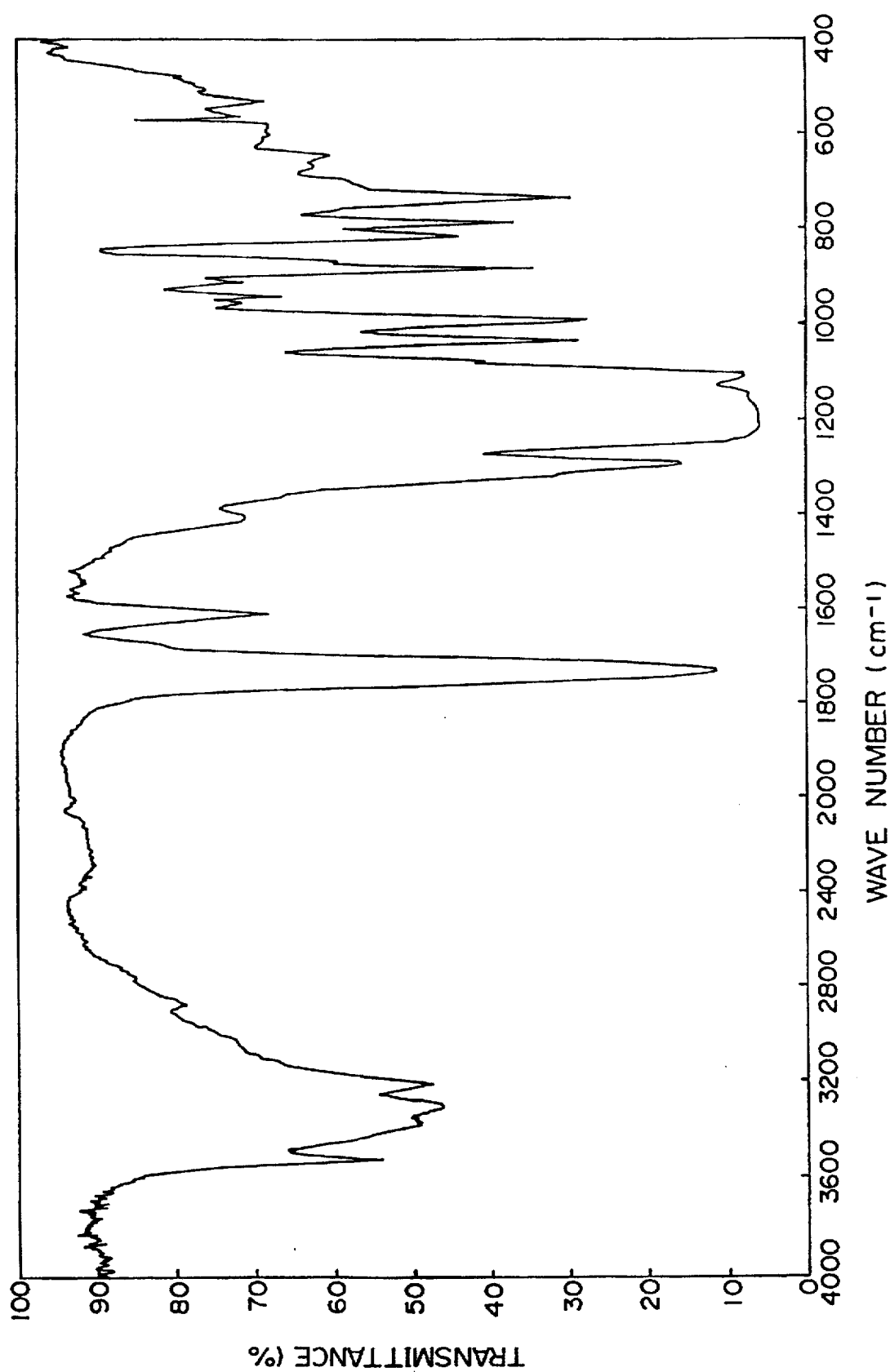
FIG. 5 is a diagram showing infrared absorption spectra of perfluoro(2-methyl-3,8-dioxa-9,10-dibromo-9-decanamide).

Boiling point: 112°–114°C. (1 Torr)
Infrared absorption spectra: see FIG. 5

(3) 108 g of the thus prepared perfluoro (2-methyl-3,8-dioxa-9,10-dibromo-9-decanamide), 150 ml of diglyme and 35.9 g of pyridine were charged into a glass flask having a net capacity of 300 ml, provided with a stirrer and a dropping funnel, and 47.8 g of trifluoroacetic acid anhydride was dropwise added thereto over one hour, while keeping the flask inside at 5° to 10° C. After the dropwise addition, the temperature of the flask inside was elevated to room temperature and stirring was further continued for 30 minutes. Then, the reaction mixture was poured into 150 ml of ice water, and the separated organic layer was washed with water and dried over magnesium sulfate, whereby 93 g of perfluoro (2-methyl-3,8-dioxa-9,10-dibromo-9-decanonitrile) was obtained (yield: 84%).

Figure 6:
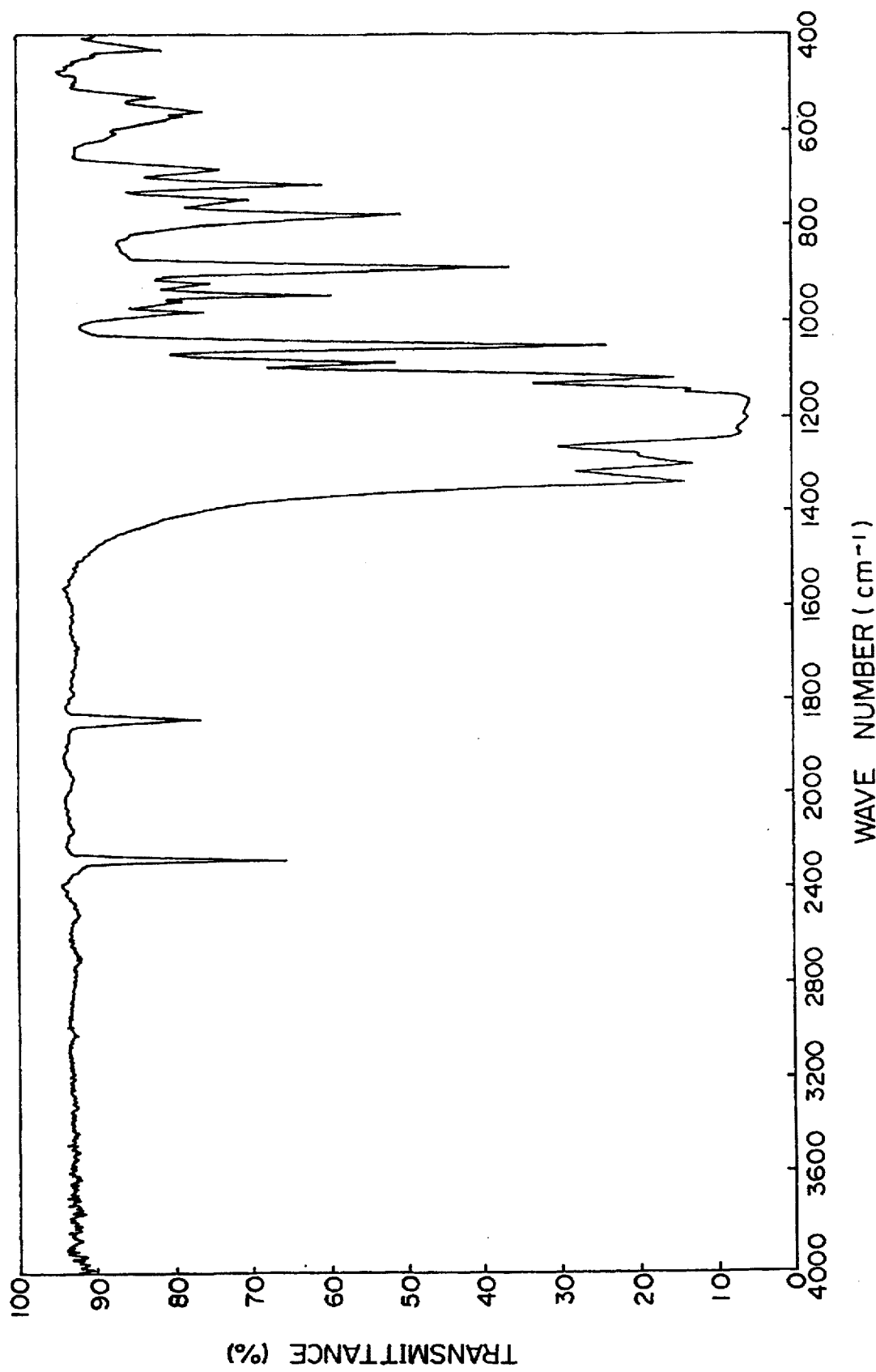
FIG. 6 is a diagram showing infrared absorption spectra of perfluoro(2-methyl-3,8-dioxa-9,10-dibromo-9-decanitrile).

Infrared absorption spectra: see FIG. 6

(4) 19 g of zinc powder, 0.3 g of zinc bromide and 150 ml of dioxane were charged into a glass flask having a net capacity of 300 ml, provided with a stirrer, a dropping funnel and a cooling pipe, and 86 g of the thus prepared perfluoro (2-methyl-3,8-dioxa-9,10-dibromo-9-decanonitrile) was dropwised added thereto over 30 minutes, while keeping the flask inside at 90° to 100° C. After the dropwise addition, a crude product mixture obtained, and then distilled over phosphorus pentoxide, whereby 54 g of perfluoro (2-methyl-3,8-dioxa-9-decenonitrile) was obtained (yield: 85%).

Figure 7:
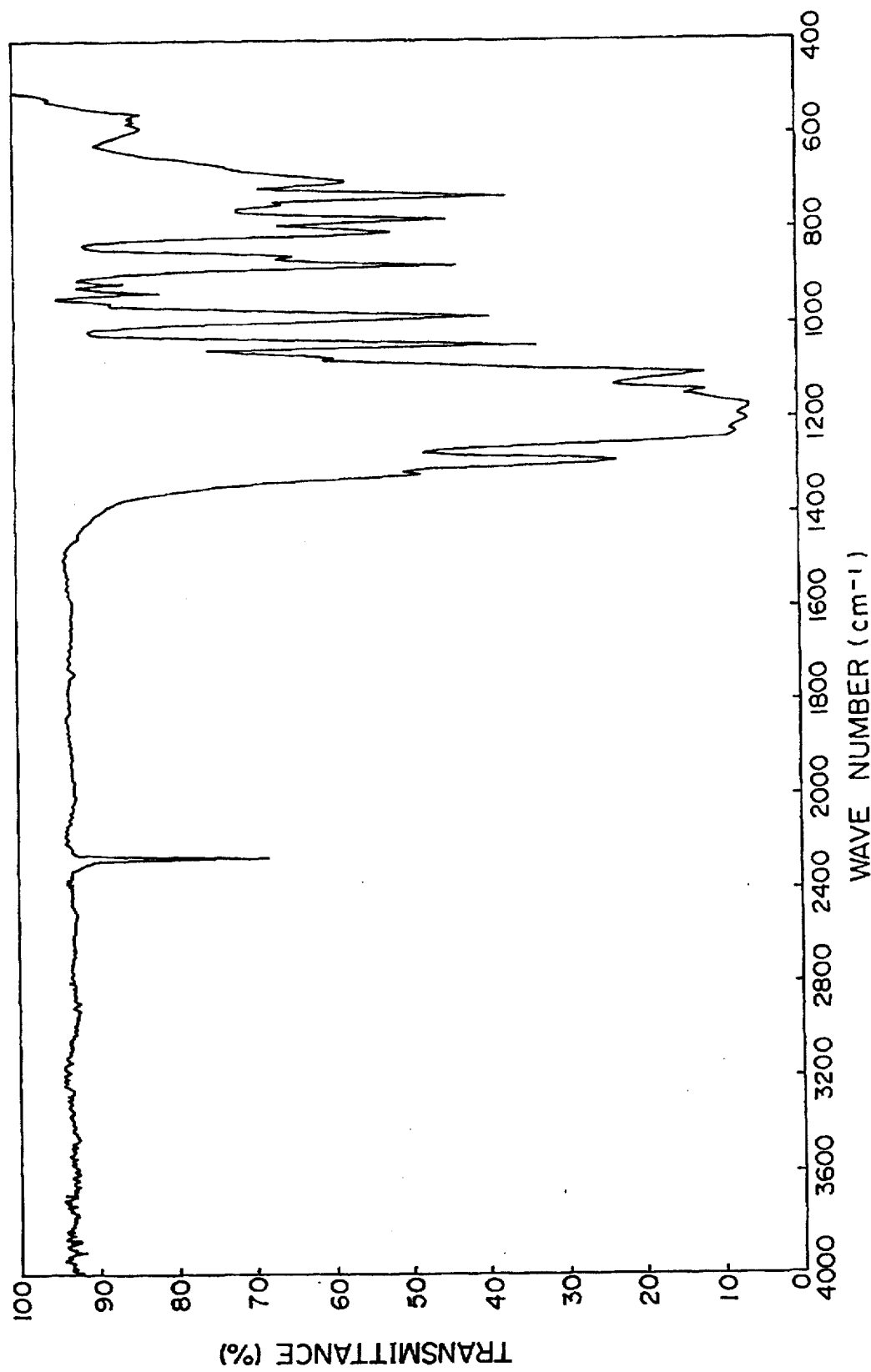
FIG. 7 is a diagram showing infrared absorption spectra of perfluoro(2-methyl-3,8-dioxa-9-decenonitrile).

Boiling point: 49°–50°C. (72 Torr)
Infrared absorption spectra: see FIG. 7
$^{19}$F-NMR (internal standard: CFCl$_3$):

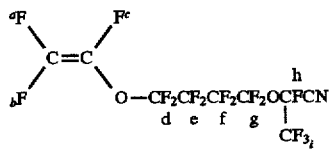

a = –113.9ppm (dd, Jac = 66Hz, Jab = 87Hz)
b = –121.4 (dd, Jab = 87Hz, Jbc = 112Hz)
c = –135.1 (dd, Jac = 66Hz, Jbc = 112Hz)
d = –83.9 (s)
e, f = –124.0 (s)
g = –79.9, –83.9 (AB,J = 153Hz)
h = –113.0 (s)
i = –88.1 (s)

What is claimed is:

1. A process for producing a perfluoro unsaturated nitrile compound represented by the following general formula:

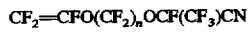

where n is an integer of 2, 3, 4 or 5, which process comprises subjecting a halogenated perfluoro saturated carboxylic acid amide compound represented by the following general formula:

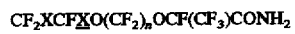

where X is a chlorine atom or a bromine atom and n has the same meaning as defined above, to a dehydration reaction, thereby forming a nitrile group and to a dehalogenation reaction, thereby forming a vinyl group, in any desired sequence.

2. A process according to claim 1, wherein the dehalogenation reaction is carried out with a dehalogenating agent in a protonic polar solvent or an aprotic solvent.

3. A process according to claims 2, wherein the dehalogenating agent is Zn, Zn/ZnCl$_2$, Zn/ZnBr$_2$, Zn/Cu or Mg.

4. A process according to claim 3, wherein Zn is used after activation of Zn surface with dilute hydrochloric acid.

5. A process according to claim 2, wherein the protonic polar solvent is methanol or ethanol.

6. A process according to claim 2, wherein the aprotic polar solvent is dioxane or tetrahydrofuran.

7. A process according to claim 1, wherein the dehydration reaction is followed by the dehalogenation reaction.

8. A process according to claim 1, wherein the dehalogenation reaction is followed by the dehydration reaction.

* * * * *